United States Patent [19]
Jardieu

[11] Patent Number: 5,112,605
[45] Date of Patent: May 12, 1992

[54] TEMPORAL GAMMA-INTERFERON ADMINISTRATION FOR ALLERGIES

[75] Inventor: Paula Jardieu, Belmont, Calif.

[73] Assignee: Genentech, Inc., South San Francisco, Calif.

[21] Appl. No.: 325,406

[22] Filed: Mar. 17, 1989

[51] Int. Cl.$^5$ ............................................. A61K 37/66
[52] U.S. Cl. .................................................. 424/85.5
[58] Field of Search ....................................... 424/85.5

[56] References Cited

U.S. PATENT DOCUMENTS 4,762,791  8/1988  Goeddel et al. .

FOREIGN PATENT DOCUMENTS

A48412/85  7/1985  Australia .
WO/01288  12/1987  PCT Int'l Appl. .

OTHER PUBLICATIONS

F. D. Finkelman et al., J. Immunol 141: 2335 (1988); "IL-4 is Required to Generate and Sustain In Vivo IgE Responses".
F. D. Finkelman et al., J. Immunol 137:3878 (1986); "Production of BSF-1 During an In Vivo, T-Dependent Immune Response".
I. M. Katona et al., J. Immunol 140:3206 (1988); "The Role of L3T4+ T Cells in the IgE Response and Immunity to *Nippostronglyus brasiliensis*".
F. D. Finkelman et al., J. Immunol 142:403 (1989); "T Help Requirements for the Generation of an In Vivo IgE Response: A Late Acting Form of T Cell Help Other Than IL-4 is Required for IgE But Not for IgG1 Production".
Coffmen et al., J. Immunol. 136:949 (1986); "A T Cell Activity That Enhances Polyclonal IgE Production and Its Inhibition by Interferon-$\gamma$".
Snapper et al., Science 236:944 (1987); "Interferon-$\gamma$ and B Cell Stimulatory Factor-1 Reciprocally Regulate Ig Isotype Production".
Coffman, et al., Immune Regulation by Characterized Polypeptides, Alan R. Liss, Inc., 523–532 (1987).
T. DeFrance et al., J. Exp. med. 165:1459 (1987); "Human Recombinant Interleukin 4 Induces Fce Receptors (CD23) on Normal Human B Lymphocytes".
S. A. Hudak et al., PNAS 84:4606 (1987); "Murine B-Cell Stimulatory Factor 1 (Interleukin 4) Increases Expression of the Fc Receptor for IgE on Mouse B Cells".
F. D. Finkelman et al., J. Immunol. 140:1022 (1988); "IFN-$\gamma$ Regulates the Isetypes of Ig Secreted During In Vivo Humoral Immune Responses".
Boguniewicz et al., J. Allergy and Clin. Immunol 83:307 (100), "In Vivo Treatment of Atopic Dermatitis (AD) with Recombinant Gamma Interferon (rIFN-$\gamma$)" (1989).
Li et al., J. Allergy and Clin. Immunol. 83:307 (543) (1989); "Recombinant Interferon Gamma in the Treatment of Allergic Rhinitis".
J. M. Parkin et al., Br. Med. J. [Clin. Res.] 294:1185 (1987); "Atopic Manifestations in the Acquired Immune Deficiency Syndrome: Response to Recombinant Interferon Gamma".

*Primary Examiner*—Howard E. Schain
*Assistant Examiner*—Choon P. Koh
*Attorney, Agent, or Firm*—Ginger R. Dreger; Carolyn R. Adler

[57] ABSTRACT

Methods for the treatment of allergic reactions are provided, wherein a pharmaceutically effective dose of gamma interferon is administered to a patient within a predetermined temporal period prior to or following exposure to an allergen.

17 Claims, 10 Drawing Sheets

TEMPORAL GAMMA-INTERFERON ADMINISTRATION FOR ALLERGIES

BACKGROUND OF THE INVENTION

This invention relates to methods for ameliorating allergic immune responses. Particularly, according to this invention, natural or recombinant gamma interferons are administered within a predetermined temporal period prior to suppress a patient's allergic immune response.

Allergy is a hypersensitivity or altered reactivity to an antigen (allergen) that can result in pathologic reactions upon the exposure of a sensitized host to that particular antigen. Although the mechanisms involved in the induction and control of allergic reactions are not completely understood, they have been classified into four types. These include immediate hypersensitivity reactions (Type I), toxic effects of anticell and antitissue antibodies (Type II), toxic effects of complexes between antibody and antigen (Type III), and delayed hypersensitivity (cell-mediated) reactions (Type IV).

In Type I, or immediate-type reactions, a variety of immunologic mechanisms may operate, but it is generally believed that they have a mediation pathway that involves the release of pharmacologically active substances from mediator cells. The antibody which is responsible for immediate hypersensitivity belongs to the IgE class of immunoglobulin. IgE antibodies bind to receptors on mediator cells such as mast cells and basophils. Once the IgE antibody is bound to the receptor, an allergen may bind to the antibody, causing the mediator cell to release granules which contain the pharmacologically active substances which lead to an allergic response.

These immediate-type reactions are triggered primarily by ingestants (food and drugs), injectants (drugs and vaccines) and inhalants (airborne organic and inorganic substances). Symptoms include hay fever, food allergies, asthma, anaphylaxis, and urticaria. Delayed-type hypersensitivity may be triggered by the same kinds of antigens, however the increased reactivity to these specific antigens is mediated not by antibodies but by T-cells. This type of reaction is seen in some autoimmune diseases, and allergic contact dermatitis.

Current therapy of allergic hypersensitivity centers on avoiding offending allergens when feasible, use of appropriate drugs to counteract the symptoms, and immunotherapy. The first approach is not always practicable, and the second is only useful on a short-term basis. Additionally, the effectiveness of drugs such as antihistamines can be limited by side effects such as drowsiness and impaired mental acuity. Similarly, the use of corticosteroids may be limited by the appearance of local and/or systemic toxicity. The use of parenteral immunotherapy has been limited by the potential for systemic allergic reactions including anaphylaxis, as well as the amount of time to reach maintenance doses and the overall duration of the therapy.

As an alternative therapeutic approach, it has been suggested to interfere in vivo with the stimuli that act on the B lymphocytes that are essential for the production of IgE. The literature demonstrating this approach are inconclusive, because the studies involve inducing polyclonal responses rather than clearly antigen-specific IgE responses. Finkelman et al., J. Immunol 141:2335 (1988); Finkelman et al., J. Immunol. 137:2878 (1986); Katona et al., J. Immunol. 140:3206 (1988); Finkelman et al., J. Immunol 142:403 (1989).

Several in vitro studies have suggested that gamma interferon inhibits the production of IgE and thus may suppress an allergic response. See, for example, Coffman et al., J. Immunol. 136:949 (1986); Snapper et al., Science 236:944 (1987); Coffman et al., Immune Regulation by Characterized Polypeptides, Alan R. Liss, Inc. 523-532 (1987); DeFrance et al., J. Exp. Med. 165:1459 (1987); and Hudak et al., PNAS 84:4606 (1987). These in vivo studies share the same basic defect as the in vivo studies discussed above, in that the involve polyclonal responses rather than clearly antigen-specific IgE responses. For example, in an in vivo study, Finkelman et al., J. Immunol. 140:1022 (1988) demonstrate that gamma interferon may suppress the polyclonal, anti-immunoglobulin, immune response in mice stimulated by the injection of a goat antibody to mouse IgD, which by itself induces large increases in levels of serum IgE and increases in other immunoglobulins.

A few studies have proposed to treat allergies by administering gamma interferon to a patient in the course of an allergic response, however these studies are anecdotal, and either inconclusive or contradictory. Australian Patent Application AU-A-48412/85 describes the administration of a gamma interferon to a patient with a food allergy. The patient received subcutaneous injections of $0.1 \times$ million I.U. of a gamma interferon formulation once a week for four weeks. It is stated that the patient's allergy was resolved after the first injection and this improvement lasted for six months after the last injection. The protocol does not indicate whether or how the patient's reaction to the antigen was challenged, or how recently before the treatment the patient had been exposed to the antigen.

PCT Application WO 87/01288 also claims the use of gamma interferon for treatment of allergies. This application appears to present the same study as Parkin et al., Br. Med. J. [Clin. Res.] 294:1185 (1987). They describe the administration of 10 and 3,000 micrograms/M$^2$ of gamma interferon to AIDS patients. While some of the patients found their allergic symptoms were apparently ameliorated, these patients also developed increased immediate and delayed hypersensitivity to common allergens. It is also indicated that other individuals in the study developed different allergic sensitivities over the course of the treatment. The observations are anecdotal, and the study provides little specific information on the challenge with the target antigen.

Two recent clinical trials of gamma interferon administration for allergies reveal contradictory data. In an anecdotal report, Boguniewicz et al., J. Allergy and Clin. Immunol 83:307 (100) (1989) disclose the treatment of 14 atopic dermatitis patients with gamma interferon. No placebo controls were included. Symptoms appeared somewhat ameliorated in some of the patients, serum IgE did not decrease, and spontaneous IgE production of peripheral blood lymphocytes decreased.

A more extensive published trail of gamma interferon with allergic patients is described in Li et al., J. Allergy and Clin. Immunol. 83:307 (543) (1989), which documents the double-blind, placebo-controlled trial of recombinant gamma interferon with forty-five adults having documented ragweed hay fever. This study seems to indicate that gamma interferon had little or no effect. There were no sinificant differences between the control and treated groups in mean weekly symptom scores, supplemental medication scores or hay fever scores, and preliminary inspection of the weekly IgE antibody measurements to crude ragweed extract suggested no marked differences among the groups.

In all of these studies, the dosages of gamma interferon and method and timing of its administration vary widely, as do the results. There remains a need for a treatment for allergies which avoids the disadvantages of the conventional methods and the inconsistencies of published methods of using gamma interferon, and yet provides effective treatment for allergic hypersensitivity.

It is an object of this invention to provide an effective therapy for patients suffering from allergies.

It is a further object of this invention to provide a means of preventing the occurrence of allergic reactions.

It is another object of this invention to increase the therapeutic efficacy of gamma interferon in vivo.

SUMMARY OF THE INVENTION

The objects of this invention are accomplished by a method comprising treating a patient known to be susceptible to an allergic response by the administration of a pharmaceutically effective dose of gamma interferon to the patient within a predetermined temporal period prior to or following exposure to an allergen, which period is sufficient to suppress the allergic response in the patient upon subsequent exposure to the allergen. Surprisingly, this method of administration was found to result in consistent suppression of IgE response.

In one embodiment, gamma interferon was administered to an animal model for hyperimmunoglobulinemia E concurrent with or within approximately 3 days following exposure to the allergen, with a resulting suppression of IgE titer.

Gamma interferon may be administered along with additional anti-allergy therapeutic agents such as antihistamines or corticosteroids. It may also be administered along with a substance synergistic with gamma interferon in immunomodulatory assays, or which has synergistic anti-tumor or anti-viral effects, such as TNF-α or TNF-β.

BRIEF DESCRIPTION OF THE FIGURES

FIG. 1 depicts the experimental schedule discussed in the Example.

FIG. 2 shows the effect of gamma interferon on IgG response.

FIG. 3 shows the enhancement by gamma interferon of primary (1°) IgE response to antigen.

FIG. 5B depicts the tertiary response with selected points of administration, and also the tertiary IgG response at the same selected points of administration.

DETAILED DESCRIPTION

Figure 1A:
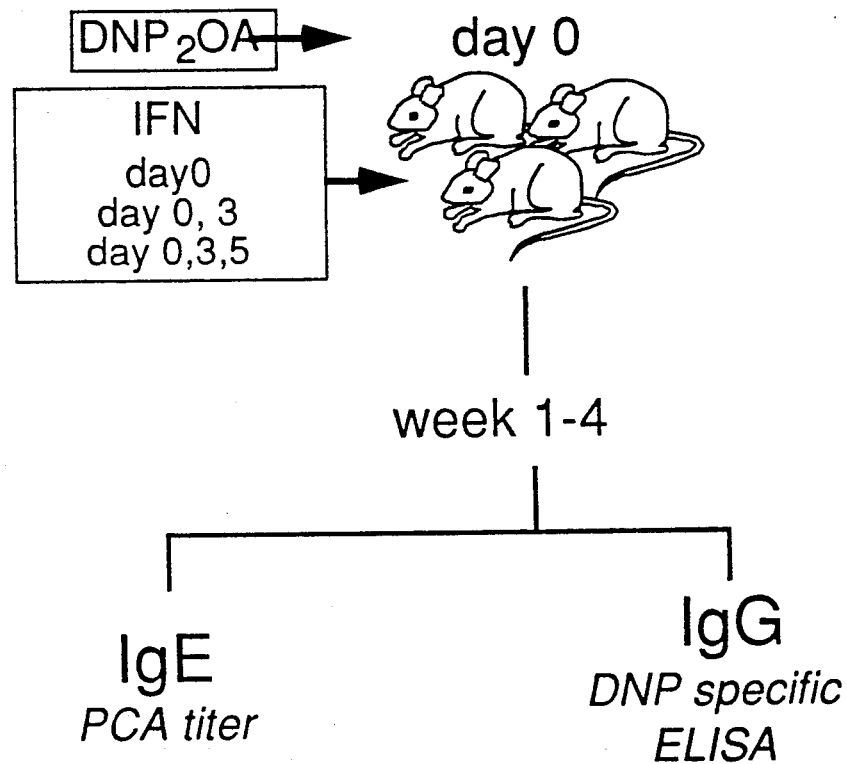
FIG. 1A shows the schedule for a primary (1°) immunization response.

As used herein, "gamma interferon" refers variously to all forms of gamma interferon as are known to be biologically active in accepted of gamma interferon assays, such as by inhibition of encephalomyocarditis virus replication in A549 cells (human lung carcinoma cell line), induction of class II antigens, heat lability, other antiviral and antitumor assays, or neutralization by antibodies having immunoreactivity for gamma interferon but not alpha- or beta-interferon, and is meant to include gamma interferon in a mature, pro, met or des (1-3) form, whether in the form of natural human gamma interferon, recombinant human gamma interferon, or related gamma interferon substances (e.g., non-human gamma interferons). A complete description of the preparation of recombinant human gamma interferon including its DNA and amino acid sequences is shown in U.S. Pat. No. 4,762,791. Amino acid, glycosylation and other variants or derivatives are included within this definition. It is expected that other variants and derivatives will become available in the future, and these are to be considered to fall within the scope of this invention.

It is currently believed that gamma interferon serves to down-regulate Interleukin-4, which is in turn involved in the up-regulation of IgE. Therefore, compositions which have the effect of down-regulating Interleukin-4, and compositions which are synergistic with gamma interferon in immunomodulatory assays, are encompassed within the scope of this invention.

TNF, as employed herein, refers, in general to the various forms of TNF which exhibit one or more biologic properties of tumor necrosis such as tumor cell lysis, inhibition of infectious agents, class II antigen induction and neutralization by antibody to TNF-α or TNF-β (lymphotoxin) but not by antibodies to other cytokines. It is believed that TNF is synergistic with gamma interferon in anti-tumor or antiviral assays for gamma interferon, and may therefore be desirably administered along with gamma interferon in the practice of this invention.

The formulations may contain agents such as antihistamines and corticosteroids previously suggested for use in allergy treatment. Gamma interferon also is suitably formulated together with known agents in order to modify or enhance the half-life or therapeutic activity of the interferon.

Gamma interferon is placed into sterile, isotonic formulations together with required cofactors. The formulation of gamma interferon is preferably liquid, and is ordinarily a physiologic salt solution or dextrose solution, together with conventional stabilizers and/or incipients. The composition may also be provided as lyophilized powder. Saline is a suitable carrier, although other conventional parenteral solutions or buffers are usable.

In a pharmacologic sense, in the context of the the present invention, a therapeutically effective amount of gamma interferon refers to that amount effective to suppress the production of IgE by the B lymphocytes. The therapeutically effective dosage of gamma interferon to be administered to a human patient generally will range from about $5 \times 10^5$ to $5 \times 10^6$ units per dose, although the dose of the gamma interferon administered will be dependent upon the species of the patient, the properties of the gamma interferon employed, e.g. its activity and biological half-like, the concentration of the interferon in the formulation, the rate of dosage, the clinical tolerance of the patients involved, the pathological condition of the patients and the like, as is well within the skill of the physician. It will be appreciated that the practitioner will adjust the therapeutic dose in line with clinical experience for any given gamma interferon.

In the practice of the invention, compositions which include a therapeutically effective amount of gamma interferon are administered to patients known to be susceptible to an allergic immune response. Accordingly, in the practice of this invention, the gamma interferon, alone or with other agents as described above, is administered to a patient within a predetermined temporal period prior to or preferably, following the exposure to an allergen, which period is sufficient to suppress the allergic response in the patient upon subsequent exposure to the allergen.

It will be understood that the critical aspect of this invention resides in appreciating that the time of administration of gamma interferon in relation to intentional or adventitious exposure to allergen is determinative of whether the IgE response to the allergen will be up-regulated or down-regulated. For each animal species and man the critical period may vary from that shown herein for a murine model, i.e. it may be greater or longer than 3 days, or it may have a more narrow window of efficacy, e.g. 1-2 days.

The exact administration parameters suitable for any given patient or animal species will be determined by routine experimentation. Typically, the patient is first exposed to allergen, e.g. by subcutaneous, oral, or inhalation administration, and thereafter gamma interferon is administered in single or clustered doses at a predetermined time. The patient is observed for symptoms of hyperallergic response and for IgE induction. If the initial study is unsuccessful another point, usually single, of temporal administration is chosen and the process repeated with that variable. It is believed that the temporal effect will be largely constant within a given species, and may be constant among species.

It is envisioned that the gamma interferon is administered as substantially a single dose, although multiple dosages are within the scope of this invention. Injections may be intraperitoneal, intracutaneous, subcutaneous, intravenous, and intramuscular. It is presently preferred to administer the gamma interferon in an aerosol suitable for inhalation.

In one preferred embodiment, a patient who has been exposed to an allergen on at least two prior occasions is exposed again to that allergen, with that exposure being concurrent with or followed within up to about three days by administration of gamma interferon.

In other embodiments, a patient who has been exposed to an allergen on at least one prior occasion is exposed again to that allergen, with the patient receiving an administration of gamma interferon within a temporal period extending from about 4 days prior and 4 days subsequent to the allergen exposure.

This invention encompasses the predetermined exposure of the patient to an allergen, including by administration of that allergen to the patient. Thus it may be seen that the method of this invention may be utilized concurrently with standard desensitization therapy.

It is also envisioned that the method of this invention may be repeated a plurality of times from about four to six weeks apart.

The method of this invention may be used to treat patients, including cats, dogs, and humans. Patients having Acquired Immune Deficiency Syndrome ordinarily are excluded from the scope of this invention. According to this invention, patients from differing species are all treated by the pharmaceutically acceptable administration of gamma interferon in a pharmaceutically effective dosage and for a period of time sufficient to ameliorate and suppress the allergic response in the patient upon subsequent exposure to an antigen.

In order that the invention described herein may be more fully understood, the following example is set forth. It should be understood that this example is for illustrative purposes only, and is not to be construed as limiting this invention in any manner.

EXAMPLE

Materials and Methods

Figure 1B:
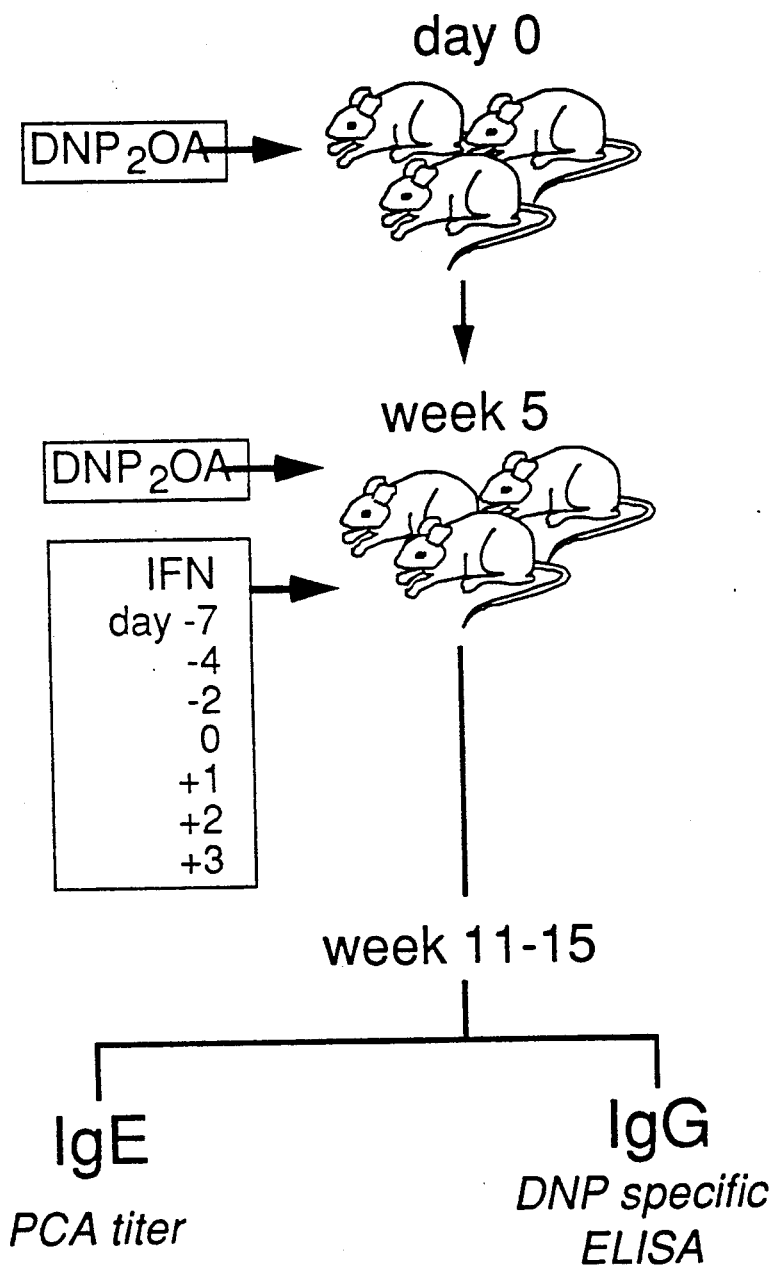
FIG. 1B shows the schedule for a secondary (2°) response.
Figure 1C:
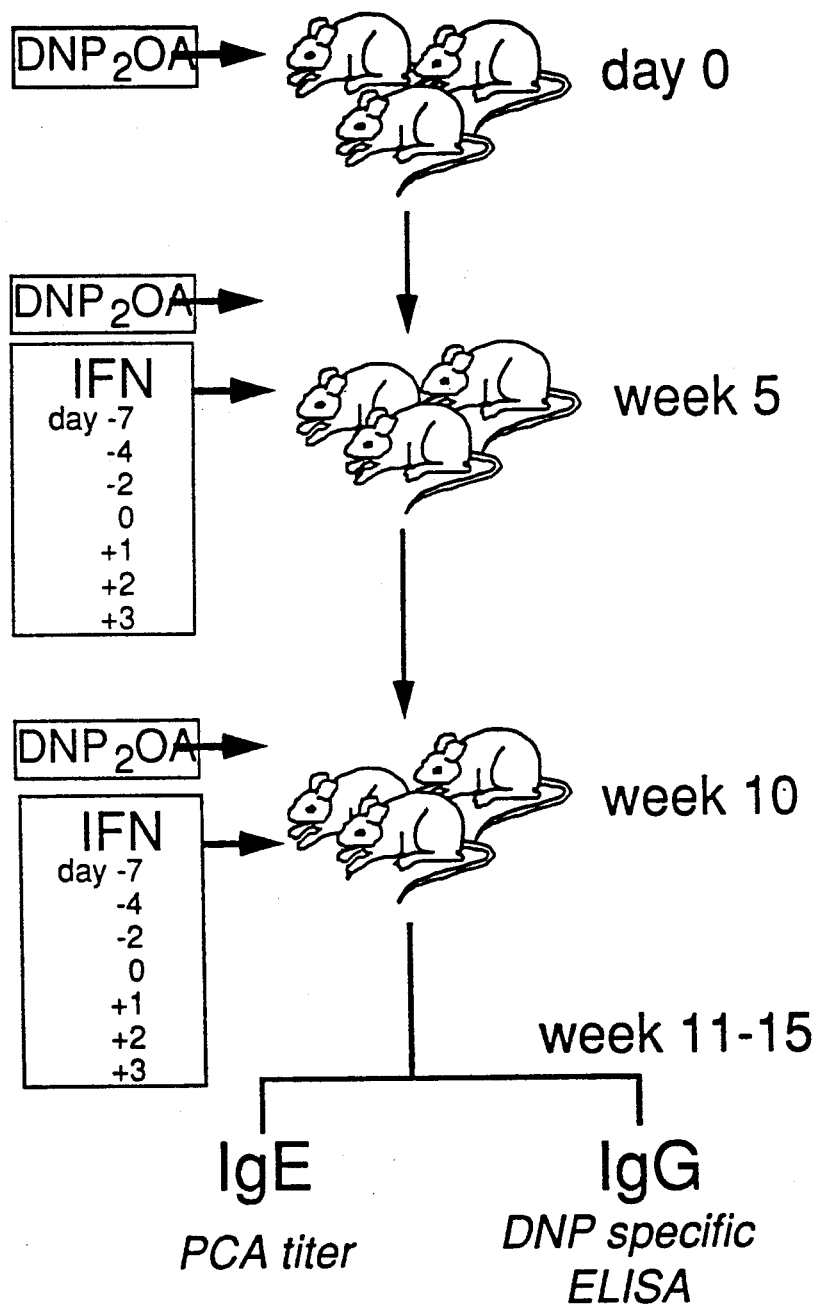
FIG. 1C shows the schedule for a tertiary (3°) response.

Immunizations: (C57BL/6×DBA/2) $F_1$ ($BDF_1$) mice were immunized by an intraperitoneal (ip) injection of 0.5 μg $DNP_2OA$ absorbed to 1 mg aluminum hydroxide gel (alum). Groups of mice were treated with $10^5$ units of recombinant murine gamma interferon by injecting 0.1 ml of the appropriate dilution ip, intramuscular (im), or intravenous (iv) as indicated in the individual experimental protocols. The experimental schedules for these experiments are shown in FIG. 1. Twenty-four animals were in each treatment group.

Measurements of anti-DNP antibodies

IgE: Anti-hapten IgE antibodies were titrated by passive cutaneous anaphylaxis (PCA) reactions in Sprague Dawley Rats. Twofold dilutions of the test mouse serum were injected intracutaneously and the reaction was elicited after a 4 hr sensitization period by an iv injection of 2.5 mg $DNP_6$-HSA (dinitrophenyl-human serum albumin) in 0.5 ml of 10% Evans Blue dye.

IgG: IgG anti-DNP antibodies in the test mouse sera were measured by an ELISA (Enzyme-linked immunoassay) using serum of anti DNP-OA primed mice as a reference standard. The ELISA was set up in 96 well plates. Each well was coated with 0.1 ml of 2.5 μg/ml $DNP_6HSA$ for 24 hrs at 4° C. After blocking with 0.1% BSA, 0.1 ml of each test sera was added to the antigen coated plates in triplicate and the plates were incubated for 2 hrs at room temperature. The plates were washed 3x with PBS/0.02% Tween 20 and 0.1 ml of a 1:2000 dilution of rabbit anti-mouse IgG (Cappel Labs) was added to each well. Plates were again incubated 2 hrs and washed. Next 0.1 ml of a 1:1600 dilution of Goat anti-Rabbit Horseradish peroxidase-conjugated antiserum was then added to each well for 1 hr at room temperature. After washing, 0.1 ml of 0.2 mg/ml OPD (orthophenyl diamine), 0.01% $H_2O_2$ in 0.05M citrate buffer was added to each well, the reaction was stopped with 2M $H_2SO_4$ after 30 minutes, and the OD was read at 490 nm on a Microtect plate reader.

Results

Primary (1°) Response

Figure 3A:
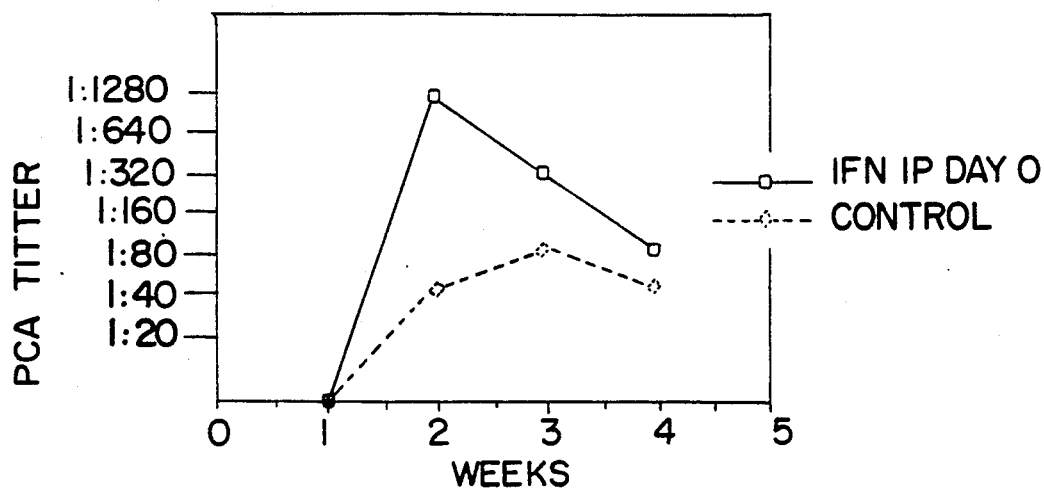
FIG. 3A shows that varying date of administration of the interferon, relative to the antigen gives varying degrees of enhancement.
Figure 3A:
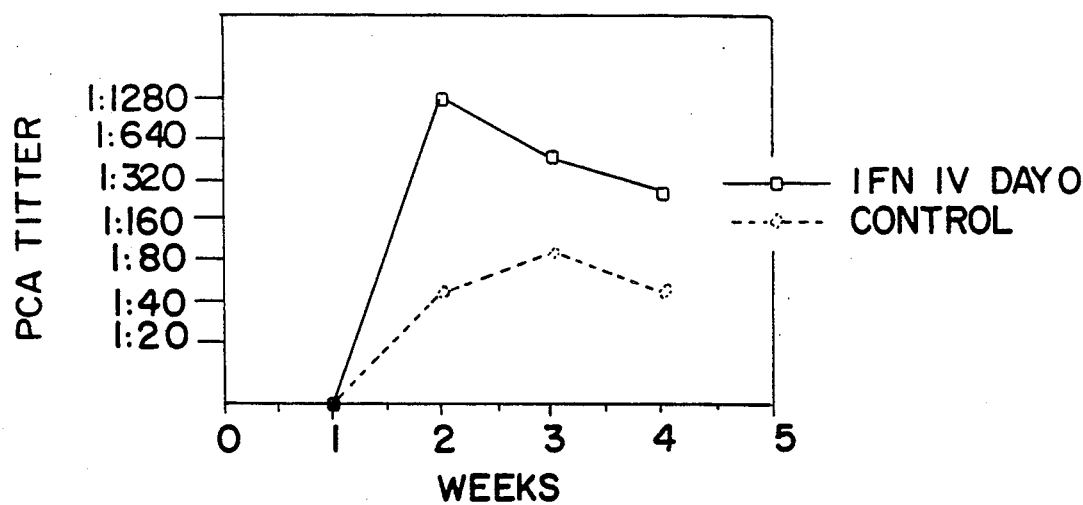
Figure 3A:
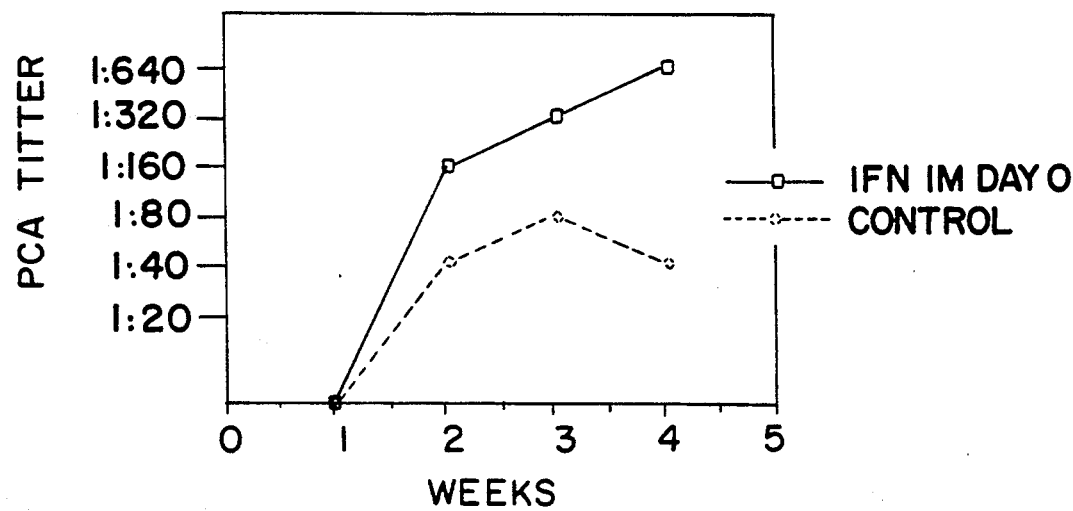
Figure 3B:
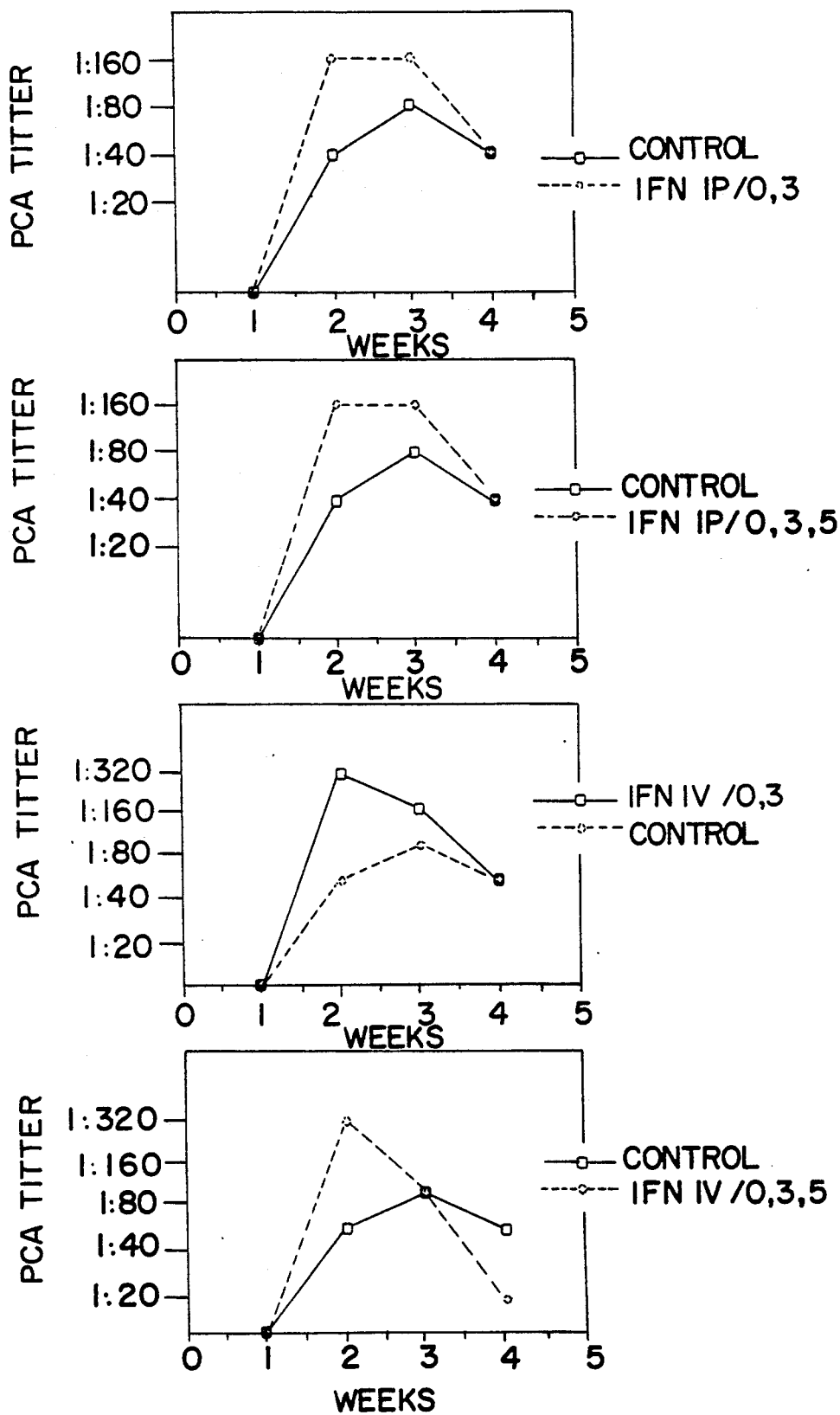
FIG. 3B shows that multiple injections of gamma interferon also enhances primary IgE response to antigen, whether given IP or IV.

As can be seen in FIG. 3A, the results of these experiments suggest that gamma interferon can augment the priming of an in vivo IgE response. This augmentation appears to be independent of the route (ip vs. im vs. iv) of injection or the number of doses (1, 2, or 3) of gamma interferon (FIG. 3B). Furthermore, if animals receive a second challenge with the antigen, the secondary (2°) IgE response is also enhanced compared to controls.

Secondary (2°)/Tertiary (3°) Response

Figure 4:
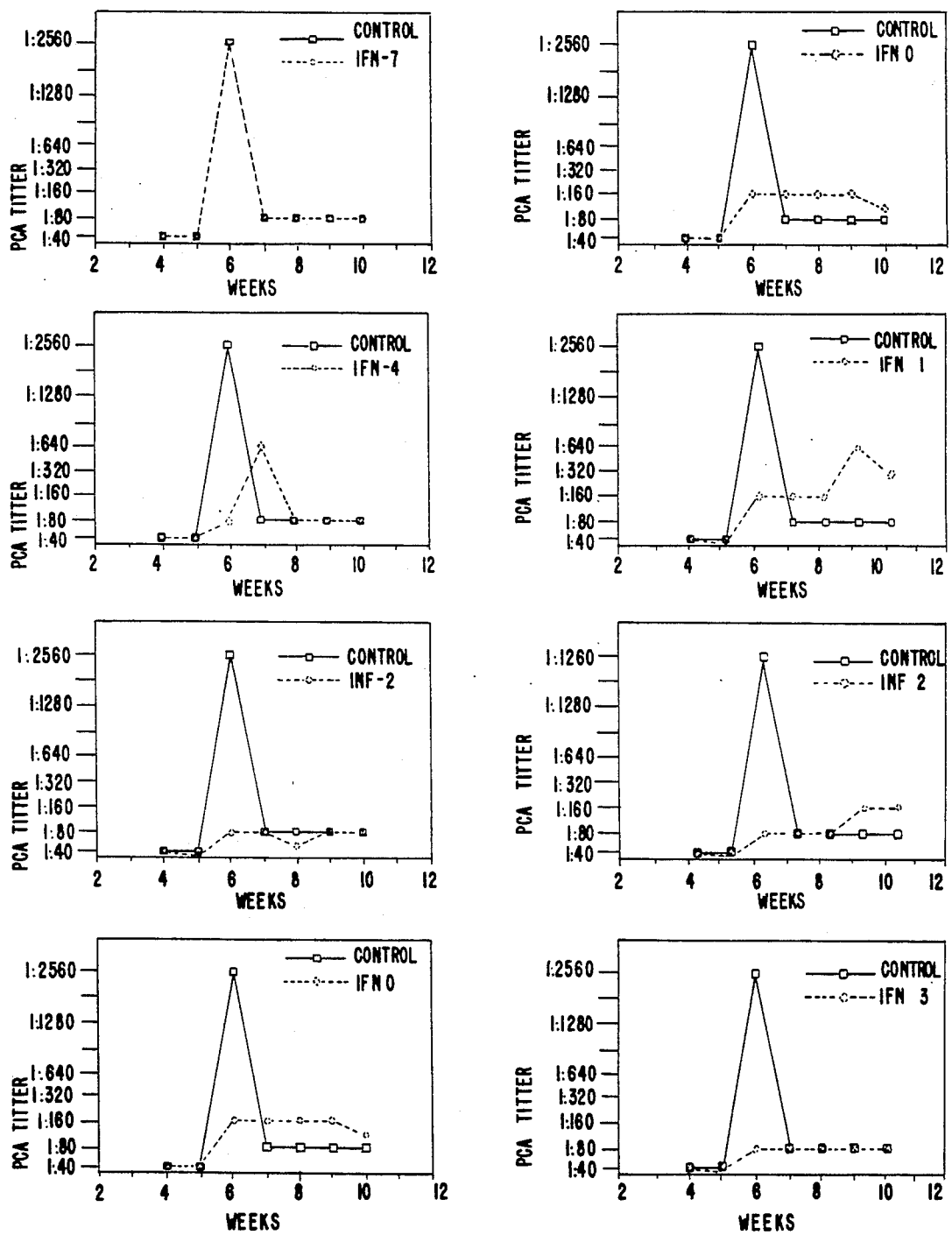
FIG. 4 shows the effect of varying temporal administration of gamma interferon on secondary IgE response to antigen.
Figure 5A:
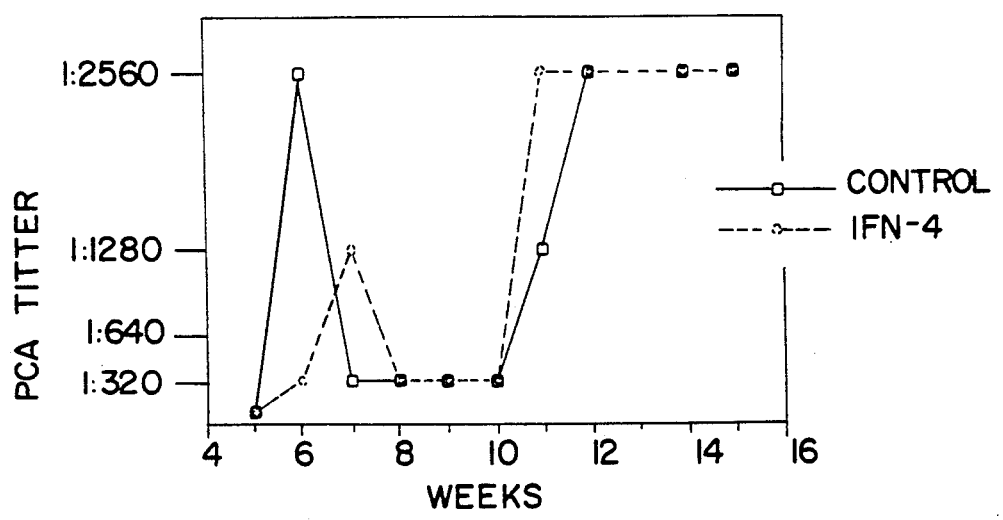
FIG. 5A and 5B show that the suppressive effect of gamma interferon on tertiary IgE response depends on the timing of administration.
Figure 5A:
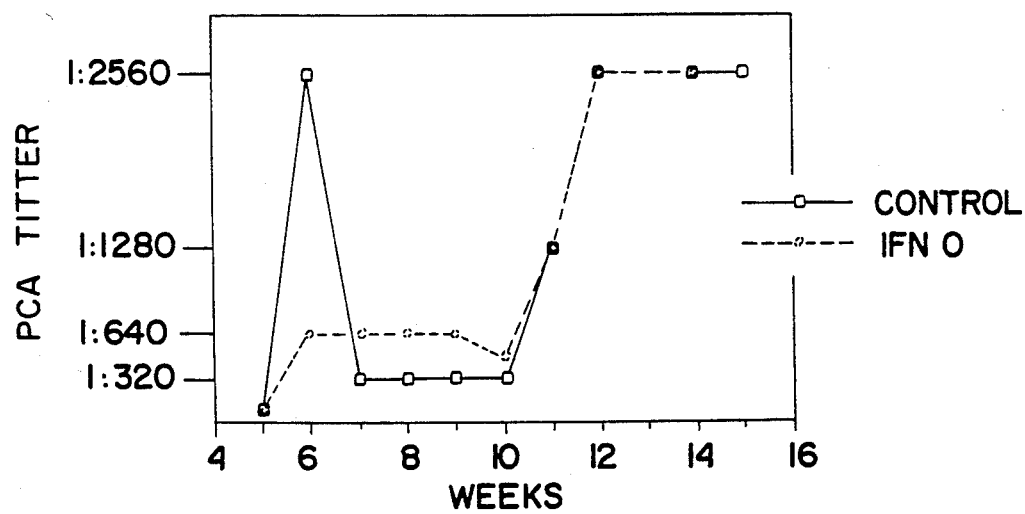
Figure 5A:
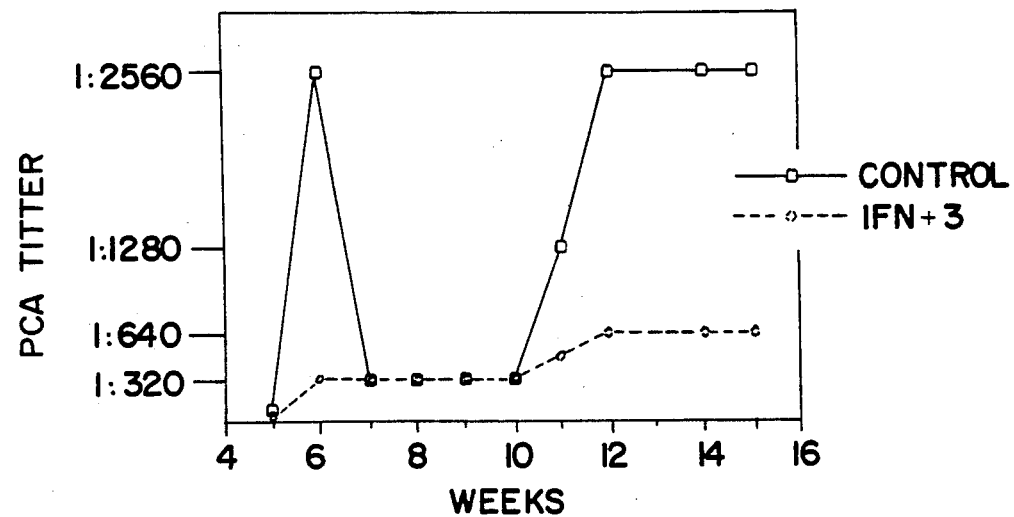
Figure 5B:
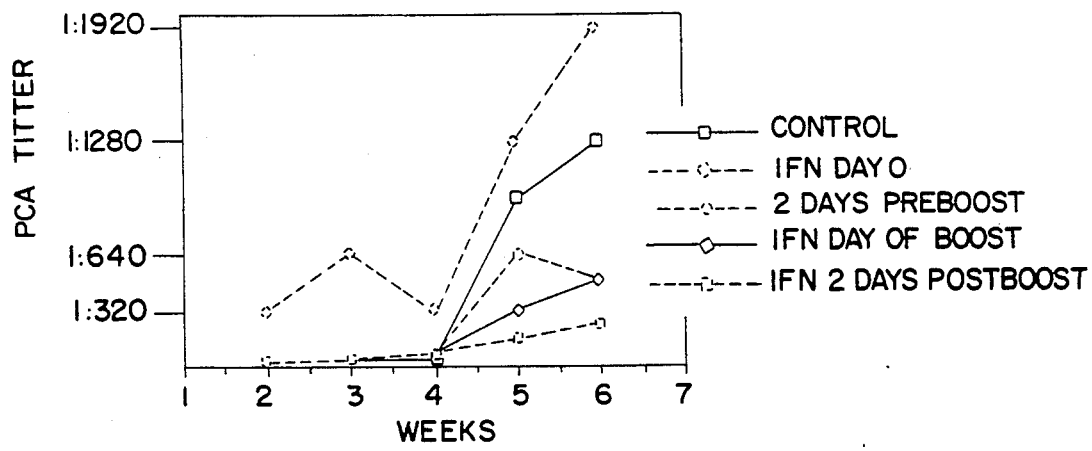
Figure 5B:
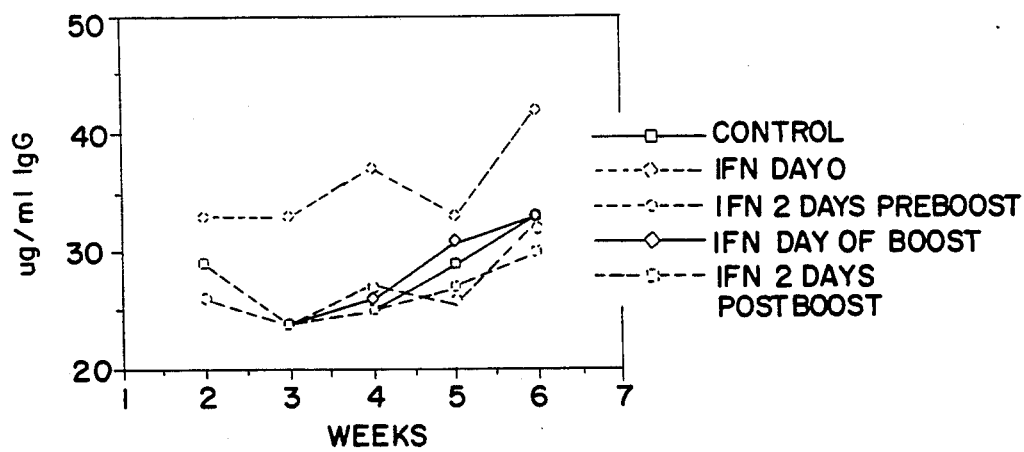
Figure 2A:
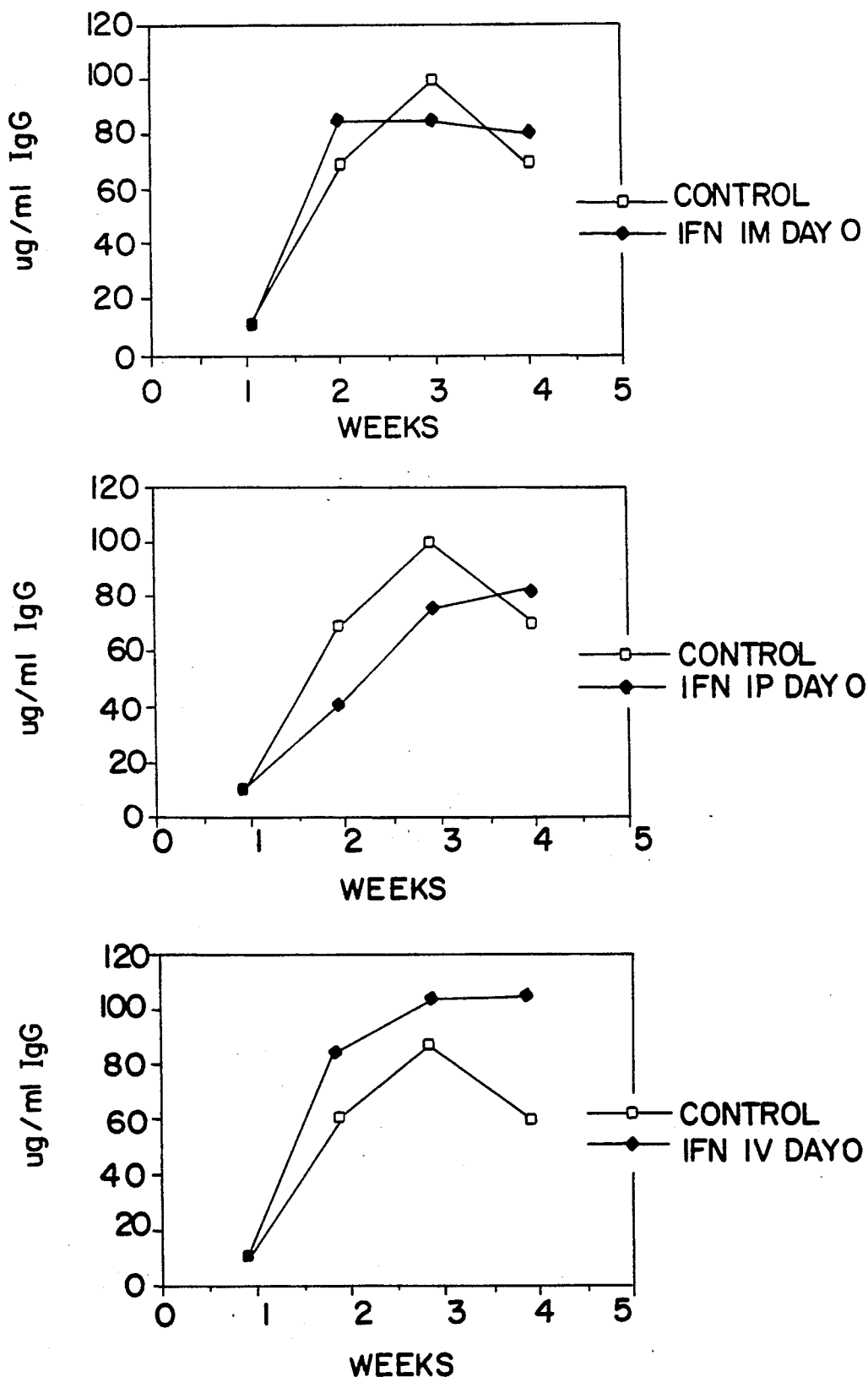
FIG. 2A shows the effect of recombinant gamma interferon (IFN) given through intramuscular (IM), intraperitoneal (IP), and intravenous (IV) delivery on primary (1°) IgG response.
Figure 2B:
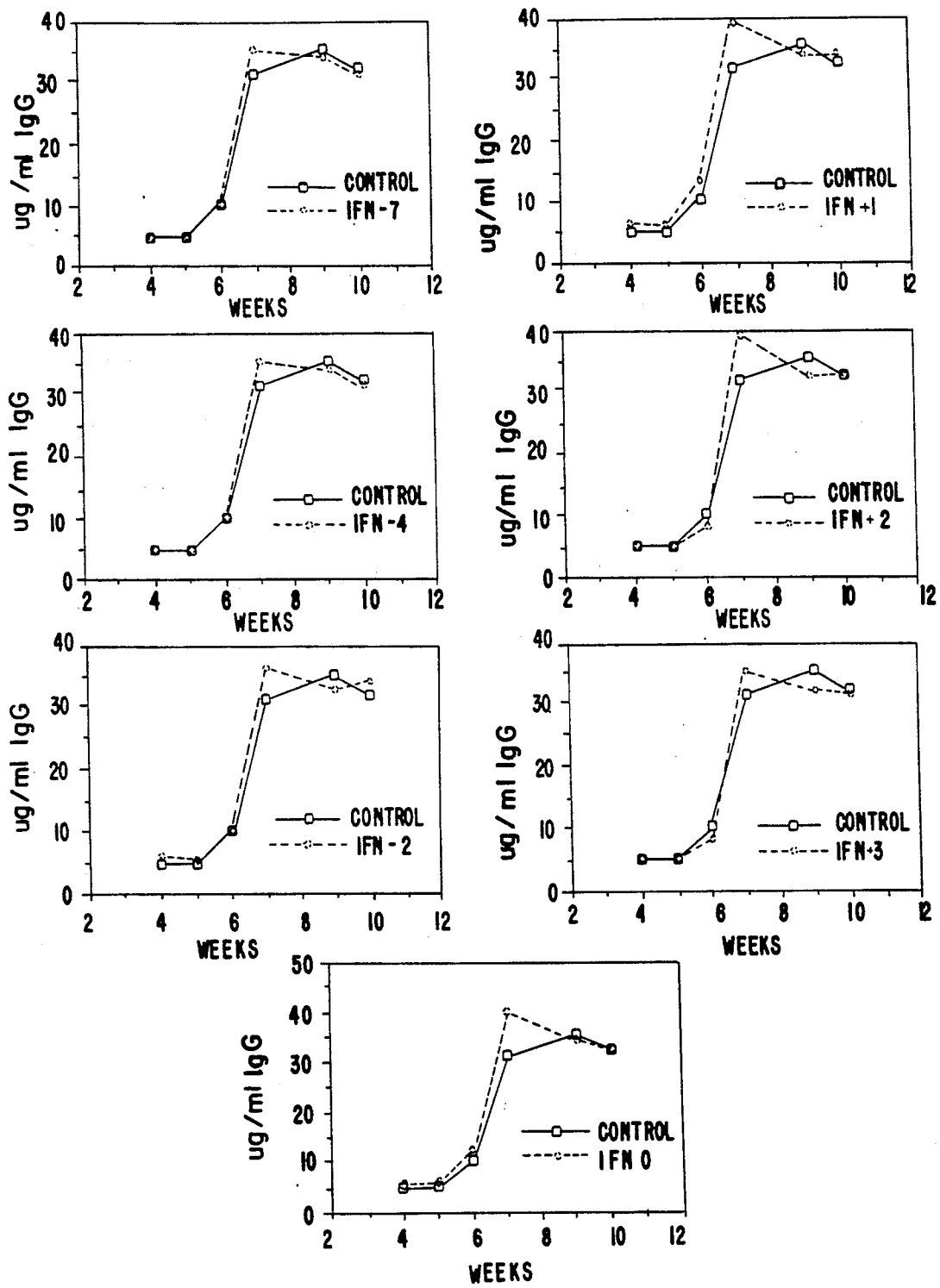
FIG. 2B depicts the secondary (2°) IgG response.

The results of these experiments suggest that gamma interferon can suppress antigen (allergen) driven IgE responses when administered in close proximity to antigen challenge. As shown in FIG. 4, in the case of the 2° response, when gamma is administered before antigen boost (0-4 days) or after boost (0-3 days), the IgE response to the antigen is significantly depressed compared to controls. In contrast, in the case of the 3° response shown in FIG. 5A, only administration of gamma interferon, after the boost (1-3 days) significantly depresses IgE responses. The clinical significance of these findings is that gamma interferon, if administered at the proper time following antigen challenge, reduces levels of IgE and therefore decreases the symptoms mediated by IgE triggering of mast cell-/basophil degranulation. In addition, since the IgG response to the antigen, shown in FIG. 5B and FIGS. 2A and 2B, is unaffected by this treatment, and allergen desensitization shots operate under the principle that these shots decrease IgE levels while increasing IgG levels, gamma interferon may be useful as an adjunct to this form of therapy.

I claim:

1. A method for the prophylaxis and amelioration of an allergic response to an allergen in a patient known to be susceptible to such response, which comprises administering the allergen to the patient followed by the administration of a therapeutically effective dose of gamma interferon within a predetermined temporal period, which period is sufficient to suppress the allergic response in such patient upon subsequent exposure to the allergen.

2. The method of claim 1 wherein the gamma interferon is administered concurrently or within approximately 0-3 days following administration of the allergen.

3. The method of claim 1 wherein the gamma interferon is selected from the group consisting of natural gamma interferon, recombinant gamma interferon, and derivatives thereof which are characterized by gamma interferon activity.

4. The method of claim 1 wherein the patient is a mammal.

5. The method of claim 1 wherein the patient is a human.

6. The method of claim 1 wherein the patient does not have Acquired Immune Deficiency Syndrome.

7. The method of claim 1 wherein the allergen is an airborne plant antigen and the gamma interferon is administered prior to the seasonal onset of the allergen.

8. The method of claim 1 wherein the therapeutically effective dose for a human patient is from about $5 \times 10^5$ to $5 \times 10^6$ units per dose.

9. The method of claim 1 wherein the allergic reaction is selected from the group consisting of food allergies, hay fever, urticaria, asthma, and spontaneous anaphylaxis.

10. The method of claim 1 wherein the gamma interferon is administered along with an additional anti-allergy therapeutic agents.

11. The method of claim 1 wherein the gamma interferon is administered along with a substance synergistic with gamma interferon in immunomodulatory assays.

12. The method of claim 1 wherein the gamma interferon is administered along with a substance synergistic with gamma interferon in anti-tumor or antiviral assays for gamma interferon.

13. The method of claim 1 wherein the gamma interferon is administered along with at least one substance selected from the group consisting of TNF-α and TNF-β.

14. The method of claim 1 wherein the gamma interferon is administered in an aerosol suitable for inhalation.

15. The method of claim 1 wherein the gamma interferon is administered intracutaneously.

16. The method of claim 2 wherein the gamma interferon is administered as substantially a single dose.

17. The method of claim 16 wherein the method is repeated a plurality of times about from four to six weeks apart.

* * * * *